United States Patent
Kuruvila et al.

(10) Patent No.: US 12,029,572 B2
(45) Date of Patent: Jul. 9, 2024

(54) METHOD OF ESTIMATING A SYSTEM RESPONSE OF AN INDIVIDUAL LISTENER'S BRAIN TO A SOUND SIGNAL STIMULUS

(71) Applicant: Sivantos Pte. Ltd., Singapore (SG)

(72) Inventors: Ivine Kuruvila, Erlangen (DE); Ulrich Hoppe, Spardorf (DE); Stefan Handrick, Erlangen (DE); Eghart Fischer, Schwabach (DE); Maja Serman, Erlangen (DE); Henning Puder, Erlangen (DE)

(73) Assignee: Sivantos Pte. Ltd., Singapore (SG)

( * ) Notice: Subject to any disclaimer, the term of this patent is extended or adjusted under 35 U.S.C. 154(b) by 892 days.

(21) Appl. No.: 17/106,442

(22) Filed: Nov. 30, 2020

(65) Prior Publication Data
US 2021/0161418 A1 Jun. 3, 2021

(30) Foreign Application Priority Data
Nov. 28, 2019 (EP) .................................. 19212300

(51) Int. Cl.
*A61B 5/377* (2021.01)
*A61B 5/291* (2021.01)
(Continued)

(52) U.S. Cl.
CPC ............. *A61B 5/377* (2021.01); *A61B 5/291* (2021.01); *A61B 5/316* (2021.01); *A61B 5/374* (2021.01)

(58) Field of Classification Search
CPC .................................................. G06F 2119/10
See application file for complete search history.

(56) References Cited

U.S. PATENT DOCUMENTS 6,343,230 B1 * 1/2002 Smits .................. A61B 5/38
600/544
8,298,140 B2 11/2012 Beck-Nielsen et al.
(Continued)

FOREIGN PATENT DOCUMENTS

CN 107864440 A 3/2018
CN 108430406 A 8/2018
(Continued)

*Primary Examiner* — Eric F Winakur
*Assistant Examiner* — Abel Seifu Abegaz
(74) *Attorney, Agent, or Firm* — Laurence A. Greenberg; Werner H. Stemer; Ralph E. Locher

(57) ABSTRACT

A system response of an individual listener's brain to a sound signal stimulus is estimated. The system response represents the generation of an electroencephalography signal measured at a given measuring point of the listener's head by the sound signal stimulus. A sound signal with the sound signal stimulus is presented to the ear of the listener. An audio signal corresponding to the sound signal is generated, and audio signal data is extracted from the audio signal with a measuring electrode that measures an electroencephalography training signal. A measurement data set is generated from the first electroencephalography training signal. A noise signal is measured on the listener's head while the first sound signal impinges on the listener's ear. A Gaussian conditional probability density function taken as the system response of the listener's brain to the sound signal stimulus, with respect to the given measurement point.

18 Claims, 4 Drawing Sheets

(51) Int. Cl.
    *A61B 5/316*    (2021.01)
    *A61B 5/374*    (2021.01)

(56) References Cited

U.S. PATENT DOCUMENTS

| | | |
|---|---|---|
| 10,362,414 B2 | 7/2019 | Lunner et al. |
| 10,893,371 B2 | 1/2021 | Hughes et al. |
| 2003/0185408 A1 | 10/2003 | Causevic et al. |

FOREIGN PATENT DOCUMENTS

| | | |
|---|---|---|
| EP | 1789907 A1 | 5/2007 |
| EP | 2238899 A1 | 10/2010 |
| EP | 2560412 A1 | 2/2013 |
| EP | 2789293 A1 | 10/2014 |
| EP | 2950555 A1 | 12/2015 |
| WO | 2007144307 A2 | 12/2007 |
| WO | 2018068402 A1 | 4/2018 |

\* cited by examiner

METHOD OF ESTIMATING A SYSTEM RESPONSE OF AN INDIVIDUAL LISTENER'S BRAIN TO A SOUND SIGNAL STIMULUS

CROSS-REFERENCE TO RELATED APPLICATION

This application claims the priority, under 35 U.S.C. § 119, of European patent application EP 19212300, filed Nov. 28, 2019; the prior application is herewith incorporated by reference in its entirety.

BACKGROUND OF THE INVENTION

Field of the Invention

The invention relates to a method for estimating a system response of an individual listener's brain to a sound signal stimulus. The system response represents the generation of an electroencephalography signal measured at a given measuring point of the listener's head by the sound signal stimulus. The invention further relates to a method for an auditory attention decoding of an individual listener's attention to one out of at least a first useful signal and a second useful signal by using an electroencephalography signal measured at a given measuring point at the listener's head. The invention also relates to a hearing aid configured to estimate the system response of the hearing aid user's brain to a sound signal stimulus.

When the human auditory system is stimulated by an acoustic signal, the response of the human brain to acoustical stimuli can be measured by electroencephalography (EEG) using respective electrodes on the listening person's head. The neural activity of the listener undergoes variations that track the changes in the acoustical stimulus with a fixed latency and similar waveforms. Such a change in the neural activity, induced by specific acoustic stimuli such as sine tones or short syllables like /da, /ta or similar, is called an auditory evoked potential (AEP), which can be measured by an electrode at the listener's head.

When the sound which serves as an acoustic stimulus for a listener contains a plurality of useful signals such as speech signals from two or more different speakers, the corresponding EEG signals measured by one or more electrodes at the listener's head can be used to infer, from correlations between the variations of each of the speech signals and the corresponding EEG signals, to which of the speech signals the listener actually is paying attention, since the changes in modulation vary over the different speech signals, and an EEG signal may show which modulation pattern, and thus, which of the speech signals is the one that is actually stimulating the neural activity of the listener. This method is called auditory attention decoding (AAD).

Since the true EEG signal related to the sound signal stimulus can be measured only for the mixture of all speech signals together, for AAD by means of EEG, an estimation of the system response of the listener's brain to a sound signal stimulus is required in order to be able to somehow simulate the neural activity that each of the individual speech signals would have provoked in the listener's brain in the absence of either of the other speech signals, for observing correlations between a truly measured EEG signal with the simulated or inferred neural reactions for each speech signal, as the speech signals may be separated from each other by sound signal processing techniques. AEP, and EEG signals related to auditory events in general, have become of increasing interest in particular in the context of hearing aids, where separating one speaker's speech out of a mixed multi-speaker sound situation is a common signal processing task.

It is accordingly an object of the invention to provide a method which overcomes a variety of disadvantages of the heretofore-known devices and methods of this general type and which provides for a method for estimating a system response of an individual listener's brain to a sound signal stimulus, which may be compatible with an AAD process to be used or applied in a hearing aid, and which shall allow for inferring an EEG signal at a given measuring point of the listener's head and related or corresponding to the sound signal stimulus. It is a further object of the invention to provide for a reliable AAD process which may also be used in a hearing aid. Finally, it is an object of the invention to present a hearing system with a hearing aid, capable of estimating a system response of an individual listener's brain to a sound signal stimulus.

With the above and other objects in view there is provided, in accordance with the invention, a method of estimating a system response of an individual listener's brain to a sound signal stimulus, the system response representing a generation of an electroencephalography signal measured at a given measuring point of the listener's head by the sound signal stimulus, the method comprising:

- presenting a first sound signal containing the sound signal stimulus to an ear of the listener;
- generating a first audio signal corresponding to the first sound signal, and extracting first audio signal data from the first audio signal;
- using a first measuring electrode at said given measuring point on the listener's head for measuring a first electroencephalography training signal while the first sound signal containing the sound signal stimulus impinges on the ear of the listener, and generating a first measurement data set from the first electroencephalography training signal;
- using a noise measuring electrode at a noise measuring point on the listener's head for measuring a noise signal while the first sound signal impinges on the ear of the listener, and generating a noise data set from the noise signal;
- deriving from the first measurement data set and the noise data set a Gaussian conditional probability density function for the system response of the listener's brain to the first audio signal data, given an observation of the first measurement data set; and
- taking the Gaussian conditional probability density function as the system response of the listener's brain to the sound signal stimulus, with respect to the given measurement point.

In other words, according to the invention, the first object is solved by a method for estimating a system response of an individual listener's brain to a sound signal stimulus, said system response representing the generation of an EEG signal measured at a given measuring point of the listener's head by said sound signal stimulus, wherein a first sound signal containing the sound signal stimulus is presented to the ear of the listener, wherein a first audio signal corresponding to the first sound signal is generated, and first audio signal data is extracted from the first audio signal, wherein using a first measuring electrode at said given measuring point on the listener's head, a first EEG training signal is measured while the first sound signal containing the sound signal stimulus impinges on said ear of the listener, and a first measurement data set is generated from the first EEG training signal, and wherein using a noise measuring electrode at a noise measuring point on the listener's head, a noise signal is measured while the first sound signal impinges on said ear of the listener, and a noise data set is generated from the noise signal.

Furthermore, in the method, a Gaussian conditional probability density function (cPDF) for the system response of the listener's brain to said first audio signal data, given the observation of the first measurement data set, is derived from the first measurement data set and the noise data set, and wherein said Gaussian cPDF is taken as the system response of the listener's brain to the sound signal stimulus, with respect to said given measurement point. Embodiments of particular advantage will be outlined in the following description and in the dependent claims.

The second object, according to the invention, is solved by a method for an AAD of an individual listener's attention to one out of at least a first useful signal and a second useful signal, wherein an ear of the listener is exposed to a first sound signal containing a sound signal stimulus, wherein a system response of the listener's brain to the sound signal stimulus with respect to said given measuring point is estimated by means of a first EEG training signal measured using a measuring electrode disposed at said given measuring point, said estimation being performed using the method described above, the sound signal stimulus being contained in said first sound signal, wherein an environment sound containing at least the first useful signal and the second useful signal is converted at said ear of the listener into second audio signal, wherein from the second audio signal, first signal contributions of the first useful signal are extracted, and wherein from the second audio signal, second signal contributions of the second useful signal are extracted.

Furthermore, the AAD method includes that from the system response of the listener's brain and the first signal contributions, a first reconstructed EEG signal is derived and from the system response of the listener's brain and the second signal contributions, a second reconstructed EEG signal is derived, wherein, while the environment sound is impinging on the listener's ear, a first EEG application signal is measured by means of a measuring electrode located at said given measurement point, and wherein from correlations between said first EEG application signal and the first reconstructed EEG signal and from correlations between said first EEG application signal and the second reconstructed EEG signal, the listener's attention to either the first useful signal or the second useful signal is inferred. The method for an AAD of an individual listener, according to the invention, shares the benefits of the proposed method for estimating the system response of the listener's brain, according to the invention. The advantages disclosed for of said method for estimating the system response of the listener's brain and for its embodiments, may be transferred to the AAD method in a straight-forward manner.

Finally, according to the invention, the third object is solved by a hearing system, comprising a hearing aid, the hearing aid comprising at least a first input transducer configured to convert a first sound signal into a first audio signal and/or at least a first output transducer to generate a first sound signal from a first audio signal, a first measuring electrode configured to measure a first electrical signal at a hearing aid user's head, the first electrical signal being indicative of a first EEG training signal stimulated by a sound signal stimulus contained in said first sound signal, a noise measuring electrode configured to measure, at the hearing aid user's head, a further electrical signal indicative of a noise signal with respect to the first EEG training signal, and the hearing system further comprising a data processing facility configured to derive the first EEG training signal from the first electrical signal, to derive the noise signal from said further electrical signal, to process said first audio signal, and further configured to estimate the system response of the hearing aid user's brain to said sound signal stimulus contained in the first sound signal by employing the respective estimation method described above, the estimation using the first audio signal, the first EEG training signal and the noise signal.

The hearing system, according to the invention, shares the benefits of the proposed method for estimating the system response of the listener's brain, and the benefits of the proposed AAD method, according to the invention. The advantages disclosed for of said method for estimating the system response of the listener's brain and for said AAD method, as well as for their respective embodiments, may be transferred to the hearing aid in a straight-forward manner. In the context of the hearing system, the noise signal shall be understood as being with respect to the first EEG training signal if it is indicative of a noise present in the measurement of the first EEG training signal. In particular, the noise signal is measured at the same time than the first EEG training signal to this end.

Regarding the method for estimating a system response of an individual listener's brain to a sound signal stimulus, said system response $\theta$ shall represent the neural activity that a sound signal stimulus s may cause in the brain of the listener, such that at a given measuring point, an EEG signal denoted by r may be measured (possibly after subtracting a reference signal measured by a reference measuring electrode from the electrical signal of the measuring electrode disposed at said given measuring point), wherein the EEG signal r is given by the convolution $s*\theta$, possibly affected by some additional noise.

The first sound signal on the one hand may be an environment sound impinging on an ear of the listener which contains an appropriate sound signal stimulus for the method and which is converted into the first audio signal by an appropriate input transducer (i.e., configured to convert sound into an electrical signal), preferably close to said ear. On the other hand, the first sound signal may be generated from the first audio signal by an appropriate output transducer (i.e., configured to convert an electrical signal into sound) located close to the ear of the listener, the first audio signal generated such that the corresponding first audio signal contains an appropriate sound stimulus, e.g., a sine tone or a sequence or superposition of sine tones.

The first audio signal data in particular comprises the acoustical information of the first audio signal, processed in a way that it may be used in the method, e.g., by down-sampling and/or truncating the data to a frame of a specific length, preferably related to the duration of the sound signal stimulus. Further or other processing, such as amplification and/or noise reduction or the like, may be applied in order to extract the first audio signal data from the first audio signal.

The first EEG training signal may be given directly by the signal of the first measuring electrode, or may be derived from said signal, in particular by subtracting an appropriate reference signal of a reference measuring electrode located at an appropriate reference measuring point. As the first EEG training signal is measured while the first sound signal containing the sound signal stimulus impinges on the ear of the listener, the EEG training signal is indicative of the neural activity of the listener's brain with respect to said sound signal stimulus. For the estimation, i.e., the "training" of the model, the first EEG training signal can be given by an AEP or an auditory event-related potential, in case the sound signal stimulus is given by a sine tone or a short syllable. The first EEG training signal can also be given by any other type of auditory event related EEG signal, caused by any kind of sound signal stimulus, in particular by a speech signal.

The first measurement data set and the noise data set may be generated from the first EEG training signal and the noise signal, respectively, by data processing such as truncating the data to a specific frame (i.e., a time window), preferably related to the duration of the sound signal stimulus, and/or down-sampling. Preferably, the first measurement data set, the first audio signal data and the noise data have the same sample rate, e.g., 64 Hz.

The noise signal is measured in order to identify the "noise" in the neural activity that is present in the first EEG training signal which is not related to the sound signal stimulus, and which cannot be removed by data processing. Since this noise is typically of statistical nature, a simple subtraction also will not improve the quality of the information contained in the first EEG training signal.

However, this statistical information of the noise data can be used in combination with the assumption that the system response and the measured neural activity both are jointly Gaussian (an assumption justified by the measurement results). This assumption is not all too obvious, given the fact that the amplitude of speech, e.g., follows a Laplacian distribution. Under this assumption, a Gaussian cPDF (i.e., a Bayesian PDF) can be formulated for the system response, given the observation of the first measurement data set. This Gaussian cPDF gives the probability of finding a particular value for the system response—which in the model is a set or vector of filter coefficients that model the neural activity—when a given set of first measurement data has been observed as a reaction to the sound signal stimulus known from the first audio signal. The Gaussian cPDF thereby takes the noise statistics as an ingredient for improving the resolution of the prediction of the system response. In fact, the usage of the noise statistics, in particular its variance, allows for an integration of noise into the underlying linear model r=s*θ (with r being the EEG signal, s the sound signal stimulus and θ the system response) under the above-mentioned Gaussian assumption.

Conventional models for relating a sound signal stimulus to an EEG signal representative of a brain's reaction to said sound signal stimulus involve, at least implicitly, a matrix equation for the "propagation" of the sound signal stimulus towards the EEG signal, the "propagation kernel" being the system response. However, such matrix-based models rely, at least implicitly, on the determination of said "propagation kernel" matrix, mostly via correlation measurements. This matrix, however, can be highly underdetermined, so in order to perform the matrix inversion for being able to predict a brain reaction to a given sound signal stimulus, either very large training data sets need to be measured, or regularization techniques have to be applied to the matrix, introducing an unwanted bias. The present invention takes a different approach, relying on a statistical model with the above-mentioned Gaussian assumption for the joint probability distribution of the system response and the measured neural activity, thus being able to infer the system response by a conditional probability, and to introduce the measured noise—which is one major problem for inverting the "propagation" of the sound signal stimulus towards a neural reaction—as respective noise statistics (e.g., in form of an additional variance term).

The Gaussian cPDF, which in particular may be obtained from the joint Gaussian probability distribution for the first measurement data set (i.e., representing the EEG signal r) and the system response θ by means of a conditional expectation value for the system response given the observation of the first measurement data set, can be taken as the estimated system response. As the system response relies in a crucial way on the first measurement data set, which in turn is taken from the first measurement data measured at the first measuring point, the system response has a predictive value for other measurements performed at that very measuring point. In order to obtain an estimation for a system response at another, different measuring point, preferably a different EEG training signal is to be measured at that different measuring point (which may contain a subtraction of a reference signal measured at a reference point), and the estimation described above is done based on the corresponding measurement data taken at the other measuring point.

Preferably, a first envelope is extracted as the envelope of the first audio signal, wherein the first audio signal data is derived from the first envelope. It can be shown that an EEG signal typically tracks the envelope of a sound signal stimulus, thus discarding information related to the phase of the audio signal does not compromise the method while lowering the data overhead.

It is of further advantage if the first audio signal data is derived from the first envelope employing a down-sampling process. In certain cases, the neural activity of interest is in particular given by the so-called delta and theta waves, which are in the 1-8 Hz regime. Thus, the time resolution of the first audio signal data may be adapted to the time resolution—in terms of sample rate—of the first measurement data set, by down-sampling.

Preferably, the first measurement data set is generated from the first EEG training signal employing a down-sampling process, and/or the noise data set is generated from the noise signal employing a down-sampling process. This takes into account that in order to properly identify the respective peaks, a sampling rate of, e.g., 8 times the frequency of the neural activity waves may be sufficient, so that the down-sampling may help simplifying the following calculations. For said delta and theta waves, this means that a sample rate of 64 Hz may be sufficient.

In an embodiment, the Gaussian cPDF for the system response of the listener's brain to the first audio signal data, given the observation of the first measurement data set, is derived from a Gaussian joint probability density function for the system response of the listener's brain and the first measurement data set. This takes into account that both the first measurement data set, as derived from the first EEG training signal, and the brain's system response, may be assumed to be Gaussian. In this case, the calculations may be simplified since the whole framework of Gaussian functions and their covariance matrices can be used.

In particular, the Gaussian cPDF for the system response of the listener's brain to the first audio signal data, given the observation of the first measurement data set, is given by an expectation value of the form $$E(\theta/r) = \mu_\theta + C_{\theta\theta} S^T (S C_{\theta\theta} S^T + C_\nu)^{-1} (r - S\mu_\theta)$$

with $E(\cdot)$ denoting the expectation value, r denoting the principal data set, θ denoting the system response of the listener's brain to the sound stimulus contained in the first audio signal data represented by a vector s, $\mu_\theta$ and $C_{\theta\theta}$ denoting the expectation value E(θ) and covariance matrix of θ, respectively, $C_w$ denoting the covariance matrix of the noise data set w, and S denoting a matrix constructed such that the vector resulting from the product S·θ, entry by entry, represents the convolution of the two vectors s and θ for different time arguments, i.e., S(j,k)=s(j−k) for s having a length of N entries and s(j)=0 for j<0 or j≥N.

As the expectation value E(θ) may be assumed to be zero, and $C_{θθ}$, the covariance matrix of θ, may be sent to the identity matrix by choice of the proper normalization and basis of θ, one can further simplify the result for the estimation for the system response θ of the listener's brain to a sound signal stimulus. This estimation yields the cPDF:

$$E(θ/r)=S^T(S·S^T+C_w)^{-1}·r.$$

In a further embodiment, a plurality of sound signal stimuli is used in order to generate a set of preliminary Gaussian cPDFs, each of which is estimated by employing the method described above and by using a different sound signal stimulus out of said plurality, wherein the system response of the listener's brain to a sound signal stimulus, with respect to said given measurement point, is derived from an arithmetical mean of said preliminary Gaussian cPDFs. This means: a plurality of preferably different sound signal stimuli $v_1$, $v_2$, . . . is presented, one after another, to the hearing of the listener. The corresponding EEG training signals to each sound signal stimulus $v_j$ are measured, likewise as the corresponding noise signals during each sound signal stimulus $v_j$. Measurement data sets $r_j$ are generated from each EEG measurement, each of which corresponding to a sound signal stimulus $v_j$, and noise data sets $n_j$ are generated from the corresponding noise signals. Audio signal data $s_j$ is generated from each sound signal stimulus $v_j$ (either from a recording of the sound signal stimulus $v_j$, or by processing and possibly down-sampling a sound signal that is presented to the hearing of the listener by a speaker/receiver). For each of the sound signal stimuli $v_j$, a preliminary Gaussian cPDF is estimated, e.g., as $E_j(θ_j|r_j)$. Finally, the system response of the listener's brain to a generic sound signal stimulus is obtained by using the arithmetical mean over the preliminary Gaussian cPDFs, e.g., average $E_j(θ_j|r_j)$ over j. Since the noise generating the noise signal is assumed to be uncorrelated to the signal, the averaging further helps to reduce the influence of noise I the estimation of the system response.

Regarding the AAD method, the AAD is performed by means of an EEG signal, measured at a given measuring point. For the AAD, the system response of the listener's brain with respect to this measuring point is required. Thus, the estimation of said system response is performed by generating the first measurement data set from a first EEG training signal, measured using a measuring electrode located at said given measuring point. Preferably, the same measuring electrode is used both for the estimation of the system response and the measurement of the first EEG application signal which is used for the correlations in the AAD framework. Then, there is no need for further calibration. When the AAD method is performed with help of a hearing aid or another hearing device, it is of advantage to use the same measuring electrode for estimating the system response and for the actual AAD. Note that, in particular, the first EEG application signal may differ from the first EEG application signal mainly by the stage of usage, i.e., either for "training" of the model (estimation stage) or for the application of the model to AAD, but preferably said two signals show no further physical or conceptual differences.

Once the required system response is known, the ear of the listener is exposed to the ambient sound, or environment sound, containing the useful signals of interest. Typically, these useful signals are given by speech contributions of individual speakers. In order to decode which of the speakers the listener is actually paying attention to, their respective signal contributions are extracted from the second audio signal representing the environment sound. This extraction may be achieved by, say, blind source separation (BSS) techniques. From the signal contributions, by using the system response, the respective reconstructed EEG signals are derived, i.e., by use of the system response of the listener's brain, which contains the information on which reaction the brain will show at the measuring point of interest to some sound signal stimulus, this information is used to infer what reaction the brain would show, within the Gaussian model, to a stimulus that would be given by the respective useful signal contributions, or some data derived thereof.

This "inferred," reconstructed EEG signal to each of the useful signals, is analyzed with respect to possible correlations with the "true" EEG measurement, i.e., the first EEG application signal, performed at the measuring point, during the time the environment sound containing the useful signals impinged at the ear of the listener. The higher the correlation with the respective reconstructed EEG signal, the more likely is the listener's attention to the underlying useful signal.

In an embodiment of the AAD method, from the first signal contributions of the first useful signal, a first useful signal envelope is extracted, and the first reconstructed EEG signal is derived from the system response of the listener's brain and the first useful signal envelope, and/or wherein from the second signal contributions of the second useful signal, a second useful signal envelope is extracted, and the second reconstructed EEG signal is derived from the system response of the listener's brain and the second useful signal envelope. Using the signal envelope allows for a more efficient calculation, as no information overhead on the phase of the first and second signal contributions is required. Preferably, the estimation of the system response is adapted, via the first audio signal data, to use a corresponding signal envelope as input when inferring a respective EEG signal from a sound signal stimulus given in a sound signal.

Preferably, an auxiliary system response of the listener's brain to a sound signal stimulus with respect to a second measuring point at the listener's head is estimated by means of an auxiliary EEG training signal measured using a second measuring electrode disposed at said second measuring point, said estimation being performed using the method described above, the sound signal stimulus being contained in said first sound signal, wherein from the auxiliary system response of the listener's brain and the first signal contributions of the first useful signal, a third reconstructed EEG signal is derived, wherein from the auxiliary system response of the listener's brain and the second signal contributions of the second useful signal, a fourth reconstructed EEG signal is derived, wherein, while the environment sound is impinging on the listener's ear, an auxiliary EEG application signal is measured by means of a measuring electrode located at said second measurement point, and wherein the listener's attention to either the first useful signal or the second useful signal is inferred taking into account correlations between said auxiliary EEG application signal and the third reconstructed EEG signal, and correlations between said auxiliary EEG application signal and the fourth reconstructed EEG signal.

This allows for the integration of EEG signals taken at more than a single measuring point. Thus, by averaging or weighing decisions on the respective correlations between the first and second reconstructed EEG signals and the respective first measurement data on the one hand and the third and fourth reconstructed EEG signals and the auxiliary EEG application signal on the other hand, the reliability of the AAD may be improved. Preferably, the auxiliary EEG application signal is processed by down-sampling to this end. Preferably, the second measuring electrode used for measuring the auxiliary EEG training signal, which, in turn is used for estimating the auxiliary system response of the listener's brain at the second measuring point, is also used for deriving the auxiliary EEG application signal used for the correlations with the third and the fourth reconstructed EEG signal.

Regarding the hearing system, the first audio signal may either be a sound signal impinging on the ear of the hearing aid user, and the first input transducer converts the first sound signal into the first audio signal, or a probe signal containing probe tones such as sines or mixtures thereof at specific frequencies, or short syllables such as /da, /ta, and the output transducer converts the first audio signal into the first sound signal. In particular, the first audio signal in both of the mentioned cases may also contain a speech signal.

The noise signal may be given by a function of said further electrical signal from the noise measuring electrode, e.g., by subtracting an electrical reference signal from a reference measuring electrode, or may likewise be directly given by said further electrical signal. In the latter case, the derivation of the noise signal from said further electrical signal in the data processing facility becomes trivial.

The data processing facility may be some micro-electronic device as a part of the hearing aid, preferably comprising a CPU and respectively addressed RAM for the calculations required for the estimation, or it may be (partially) implemented on an external device, e.g., a mobile phone, which is in data connection with the hearing aid. In the latter case, a part of the data processing facility is located in the hearing aid in order to derive the mentioned signals, and one part of the data processing facility is located in the external device, for performing the calculations of the estimation of the system response. The generation of the first measurement data set, the noise data set and the first audio signal data from the corresponding signals can then be implemented in either of the parts of the data processing facility. The data processing facility in particular shall also comprise all kinds of signal processing electronics for generating the required signals which are not implemented in the main signal processing unit of the hearing aid, for example, in the form of ASICs or the like.

In an embodiment for the hearing system, the data processing facility is further configured to derive a first EEG application signal from the first electrical signal, and to perform the method for AAD of the hearing aid user's attention to one out of at least a first useful signal and a second useful signal described above, by using the first EEG application signal, when an environment sound containing the first useful signal and the second useful signal is converted into the first audio signal. The application of AAD to hearing aids is very beneficial in the framework of hearing aid signal processing, as it allows for a specific treatment of a useful signal, according to whether or not the hearing aid user is directing the attention towards said useful signal.

In particular, the data processing facility is further configured to process the first audio signal by enhancing the first signal contributions when the auditory attention decoding as a result yields the hearing aid user's attention to the first useful signal. The enhancement may be implemented, e.g., by BSS techniques, or by beam forming, if the hearing aid comprises more than one input transducer.

In an embodiment, the hearing aid of the hearing system comprises a reference measuring electrode, configured to measure an electrical reference signal at a reference measuring point on the listener's head, wherein the data processing facility is configured to derive the first EEG training signal and/or the first EEG application signal from the first electrical signal and the electrical reference signal, preferably as a difference signal, and/or the noise signal is derived from said further electrical signal of the noise measuring electrode signal and the electrical reference signal, preferably as a difference signal. Using said electrical reference signal allows for better averaging out systematical "common-mode" fluctuations.

In an embodiment, the hearing aid of the hearing system comprises an ear hook configured to be worn at least partially behind the pinna for said ear and an earpiece with a mold configured to be at least partially inserted into the concha and/or outer ear channel of an ear of the hearing aid user, wherein the first measuring electrode is disposed on the ear hook such that the first measuring electrode is in contact with the hearing aid user's scalp, preferably behind the pinna or above the transition of the pinna to the scalp, when the ear hook is worn at least partially behind the pinna. In particular, the hearing aid may be of the BTE type, and/or the ear hook may comprise a housing for electronical components, the first measuring electrode being disposed at a lateral surface of said housing. The use of an ear hook allows for separating the first measuring electrode from the noise measuring electrode, thus reducing systematical correlations between the noise signal and the first EEG training and application signals. Preferably, a grounding is also located on the mold.

In another embodiment, the noise measuring electrode is disposed on the mold of the hearing aid such that the noise measuring electrode is in contact with the skin of the concha or the outer ear channel when the mold is inserted accordingly. This yields a high spatial separation of the noise measuring electrode and the first measuring electrode.

In an alternative embodiment, the noise measuring electrode is disposed on the ear hook of the hearing aid, spatially separated from the first measuring electrode and such that the noise measuring electrode is in contact with the hearing aid user's scalp, preferably behind the pinna or above the transition of the pinna to the scalp, when the ear hook is worn at least partially behind the pinna. This may be advantageous where the space on the mold is not sufficient for hosting the noise measuring electrode, and possibly a reference measuring electrode.

In accordance with a concomitant feature of the invention, the reference measuring electrode is disposed on the mold of the hearing aid such that the reference measuring electrode is in contact with the skin of the concha or the outer ear channel when the mold is inserted accordingly.

Other features which are considered as characteristic for the invention are set forth in the appended claims.

Although the invention is illustrated and described herein as embodied in a method for estimating a system response of an individual listener's brain to a sound signal stimulus, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 1:
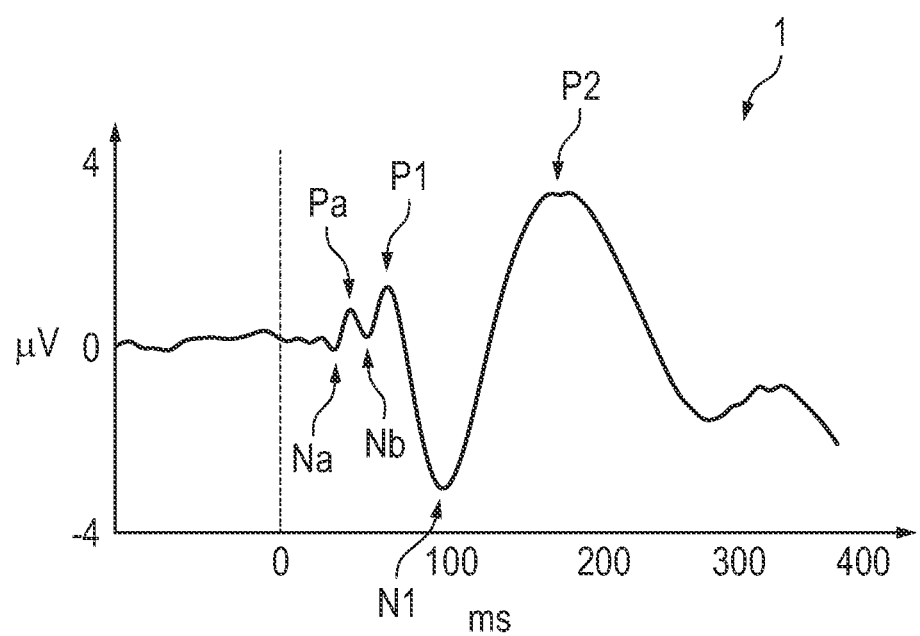
FIG. 1 schematically shows a diagram of an AEP corresponding to a sine tone.

Elements, components, and values that correspond to each other are labeled with the same references throughout the drawing.

DETAILED DESCRIPTION OF THE INVENTION

Referring now to the figures of the drawing in detail and first, in particular, to FIG. 1 thereof, there is shown a schematic illustration of an AEP 1 evoked by an audible sine tone (e.g. at a frequency of 1 kHz), as it can be measured, e.g., via ensemble averaging of an EEG measurement by an appropriate measuring electrode located at the head of the person listening to the sine tone. The AEP 1 is depicted in a diagram of measured μV over time in ms. At a time t=0 ms, the sine tone is activated. As can be seen from FIG. 1, there are small fluctuations in the EEG signal that measures the AEP 1, before the sine tone starts at 0 ms. After the sine tone starts at 0 ms, the EEG signal slowly starts to show positive and negative peaks with increasing intensity. At 25pprox . . . 30 ms, a first small negative peak, denoted by Na, can be noted in the EEG signal, followed by a first small positive peak denoted by Pa at 25pprox . . . 40 ms. Another pair of a negative peak Nb at 25pprox . . . 50 ms and a positive peak P1 at about 60-65 ms follows, where the intensities of these two peaks are already higher than the intensities of the initial negative and positive peaks Na, Pa.

Close to 100 ms after the sine tone sets in, a pronounced negative peak N1 with an intensity of close to −4 μV, about an order of magnitude more than for the previous negative peaks Na and Nb, can be measured. This negative peak N1 is followed by a pronounced positive peak P2 with an intensity of close to +4 μV, at 25pprox . . . 160-170 ms. The temporal duration of the positive peak P2 is longer than the previous peaks, so that an exact moment for this peak's maximum is more difficult to determine.

As can be seen from FIG. 1, in the measured EEG signal, there is a clear alternating pattern of negative peaks Na, Nb and N1 and positive peaks Pa, P1 and P2 of increasing intensity that follows the acoustical stimulus of the sine tone setting in at 0 ms. This pattern displays the AEP evoked by the sine tone as a sound signal stimulus. If the sound stimulus changes, i.e., if the frequency or in particular the amplitude of the sound signal experiences a substantial change, such a change can also be seen in the respective AEP, with a certain time lag between 30 ms and 200 ms for the respective positive and negative peaks, as seen in FIG. 1.

Figure 2:
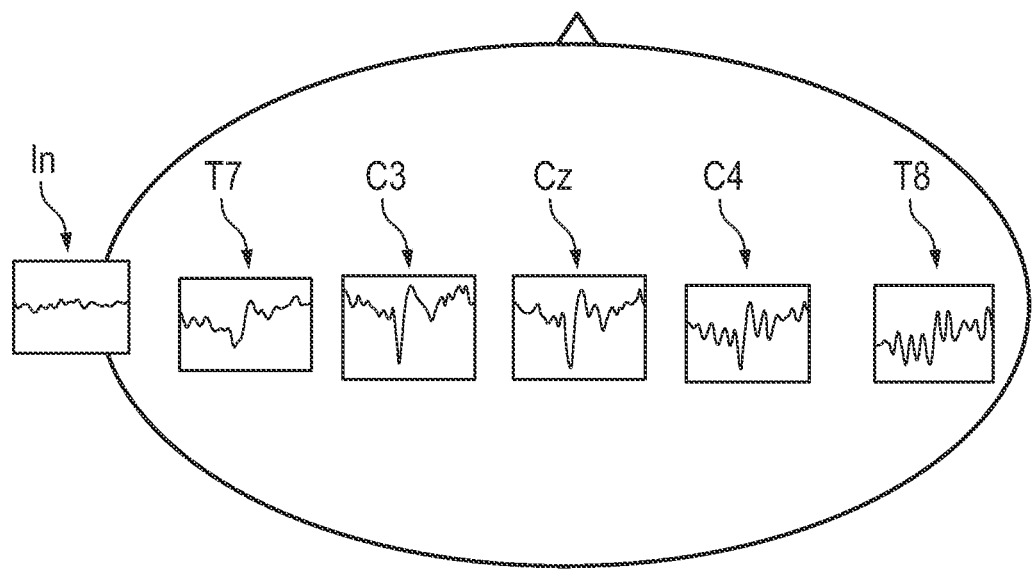
FIG. 2 schematically shows a set of various AEP signals measured by respective measuring electrodes on a human head, during a sound signal stimulus.

Note that the exact shape of a measured AEP also depends on the specific neural activity at the point of the listener's head where the measuring electrode for the EEG is located. This is shown in FIG. 2: Six different AEP measurements, taken with measuring electrodes at different locations In, T7, C3, Cz, C4 and T8 on a human head, are shown. The measuring points are located on an arch along the coronal plane on the listener's scalp from the left ear to the right ear, with T7 and T8 being positioned close to the ear, and Cz representing the "peak" of the human head. The location In corresponds to a measuring electrode positioned inside the listener's ear, preferably at the outer ear channel, close to the transition to the concha.

The measurements at the six measuring points In, T7, C3, Cz, C4 and T8 correspond to the AEPs obtained in reaction to the sine tone used for the example displayed in FIG. 1, i.e., in each of the six EEG measurement diagrams displayed in FIG. 2, a sine tone with a frequency of 1 kHz starts at t=0 ms.

It can be seen that at measuring points T7, C3, Cz, C4 and T8, an AEP comparable to the one shown in FIG. 1, is visible at least to some extent. Each of the mentioned five diagrams shows a sharp transition from a pronounced negative peak—representing the minimum voltage measured at each location—towards a pronounced positive peak which is at least close to the maximum voltage measured at each location. This transition, for all the five measurements in question, starts at the negative peak somewhat close before 100 ms and finishes at the positive peak somewhat before 200 ms. Hence, this transition can be identified as the transition from N1 to P2 in FIG. 1. The only measuring point at which no neural reaction, not the least trace of an AEP can be measured is the inside-the-ear measuring point In. This indicates that the measurement signal measured at the measuring point In inside the ear channel essentially is the noise present in the system.

Note that for the measurement performed on top of the head, i.e., at the location Cz, the measured voltages reach from −10 μV to +5 μV, i.e., cover a total difference of 15 μV, while the voltage range of C3 and C4 is slightly lower (27pprox . . . 10-12 μV), and at the "outer" measuring points T7 and T8, the total voltage range covers only 27pprox . . . 6 μV (−3 μV to +3 μV for T7 and −2 μV to 4 μV for T8).

The foregoing shows that, in order to determine an AEP, e.g., for an AAD, the measurement point Cz would be beneficial. However, such a measurement is not practical for use in combination with a normal hearing aid, as it would require a specific bow-like head-set with the measuring electrodes along the bow to be worn by the hearing aid user. The smaller the EEG signal for measuring the AEP, however, typically the more affected by noise will be the EEG signal, such that the use of signals obtained close to the ear, such as the signals from the measuring points T7 and T8, will be normally difficult in the framework of AAD. Since for AAD, normally a kind of model for inferring some hypothetical AEP to signal components extracted from a real audio signal (representative of the sound a listener is hearing at the moment of the AAD) is required, such a model is typically developed on the basis of real AEP measurements at a given measuring point. Thus, a low signal quality—in terms of the noise contained in the signal (i.e., the SNR)—deteriorates the model, and thus, the total AAD procedure.

Figure 3:
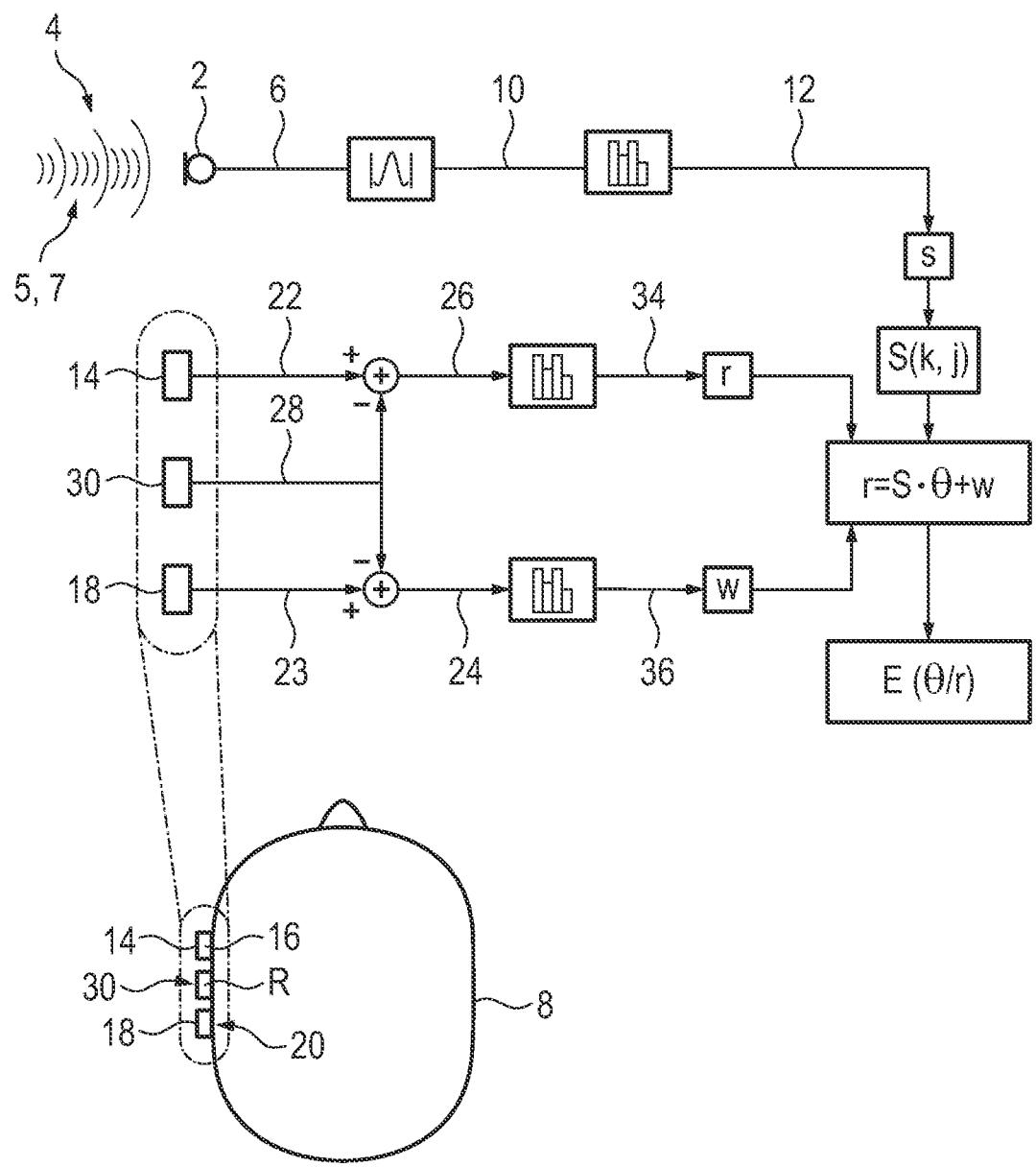
FIG. 3 a block diagram of a method for estimating the system response of a listener's brain to an acoustic stimulus by 24pprox.24 g an EEG signal and a noise signal, using a Gaussian cPDF approach.

In order to solve this problem, and to make AAD more applicable to hearing aids, an improved method for estimating the system response of a listener's brain to a signal sound stimulus is shown with help of a block diagram given in FIG. 3. In the process shown, a first input transducer 2 picks up a first sound signal 4 and converts it into a first audio signal 6. The first sound signal 4 contains an appropriate and well-defined sound pattern 5 of short length (e.g., 1-3 s) and well-defined frequency spectrum (such as a sine tone or a musical tone with its harmonics, but also an short part of a speech signal) as a sound signal stimulus 7 dominating the first sound signal 4. Thus, the neural activity at the head 8 of a listener (only partially shown) of said first environment sound 4 can be triggered, and an EEG signal may be measured accordingly in a way to be explained below. The first audio signal 6 is digitized (not shown), and a first envelope 10 is extracted from the first audio signal 6, said first envelope 10 is down-sampled at 64 Hz in order to generate the first audio signal data 12. The first envelope 10 may be extracted from the first audio signal 6 by using a Hilbert transform over an appropriate time window, or by merely taking the absolute value of the first audio signal 6.

In an alternative embodiment, the sound signal stimulus 7 may be generated by an acoustical probe signal, e.g., consisting of a sine tone or a set of musical tones with their harmonics, or of the aforementioned speech signal, of a given length. In that case, the first audio signal is given by said acoustical probe signal, which is converted into the first sound signal 4 by an output transducer (not shown) close to an ear (or at or inside an outer ear channel) of the listener.

At the head 8 of a listener, a first measuring electrode 14 is located at a first measuring point 16, and a noise measuring electrode 18 is located at a noise measuring point 20. The positioning of said first and noise measuring electrodes 14, 18 at their proper first and noise measuring points 16 and 20, respectively, may be achieved by positioning one single device that contains both of the mentioned electrodes 14, 18 at its surface, at the head 8 of the listener. In the present embodiment, such a device is given by a hearing aid (not shown) of the BTE type, the first measuring electrode being disposed on an outer surface of the ear hook housing to be worn behind a hearing aid user's ear, e.g., such that the first measuring point 16 corresponds to one of the measuring points T7 or T8 of FIG. 2, and the noise measuring electrode being disposed on an ear mold to be at least partially inserted into the outer ear channel of said hear of the use, e.g., close to the reference measuring point R of FIG. 2.

The first electrode 14 generates a first electrical signal 22, while the noise measuring electrode 18 generates a further electrical signal 23. From the first electrical signal, an EEG signal is derived which serves as a first EEG training signal 26. In the present embodiment, this is achieved by subtracting an electrical reference signal 28 from the first electrical signal 22, the electrical reference signal 28 being measured by a corresponding reference measuring electrode 30 located at a reference measuring point R, at the listener's head, preferably at or close to his outer ear channel. Also different methods for generating the first AEP 26 from the first electrical signal 22 may be implemented. The noise signal 24 is obtained as a difference signal of the output signal of the noise measuring electrode 18 and the electrical reference signal 28. The difference signals, i.e., the first EEG training signal 26 and the noise signal 24, in this embodiment are obtained via operation amplifiers (not shown) which amplify the difference of their respective input signals. Alternative methods to obtain the noise signal may be used. Furthermore, a ground electrode (not shown) may be employed for the use of the operation amplifiers of the present embodiment.

Both the first EEG training signal 26 and the noise signal 24 are down-sampled at 64 Hz in order to generate a first measurement data set 34 (from the first EEG training signal 26) and a noise data set 36, respectively. The down-sampling to 64 Hz takes into account that the neural activity of interest for AAD are the so-called delta and theta oscillations, fluctuating only up to 8 Hz, such that a temporal resolution eight times higher is supposed to suffice for EEG signals in order to identify the relevant peaks. A higher temporal resolution then does not make any sense in the first envelope 10, either.

The first measurement data set 34 now basically is a large vector r with the down-sampled EEG difference signal voltages from the first EEG training signal 26 as its entries, while the noise data set 36 is a large vector w with the respective voltages from the noise measuring electrode 18 as its entries. Accordingly, the first audio signal data 12 is a vector s with the amplitudes (i.e., signal voltages) of the down-sampled first audio signal 6 as entries. For further processing, the vectors s and w are truncated to a length of N samples, preferably in the order of magnitude of e.g. 192 samples (corresponding to 3 seconds of sound). In particular, the vectors s and w may be truncated to the length of the sound signal stimulus 7. A model for the system response of the brain of the person listening to the first sound signal 4 has to be developed now. As it can be seen from FIGS. 1 and 2, the most important parts of the neural reaction to an onset of a sound signal stimulus at 0 ms occur during the first 300-400 ms. Thus, 300 ms or 400 ms after the sound signal stimulus 7 has finished, the neural activity, and thus, the entries in the vector r will slowly vanish, or at least lose their correlation with the sound signal stimulus given by the sound signal stimulus 7. Thus, one may consider the system response as a linear filter given by a coefficient vector θ whose length p shall correspond to the assumed maximal response time (in this case, 300-400 ms, which corresponds to some 20-25 filter coefficients, i.e., "samples" for θ), and which is to be convoluted with the vector s of the first measurement data set 12, affected by the noise represented in the vector w. Thus, a considerable neural reaction related to the sound signal stimulus 7 may only be visible in the first measurement data set 12, i.e., in the entries of the vector r that correspond to maximally the length of the sound signal stimulus 7 plus the assumed "length" of the brain's system response θ, i.e., r may be truncated to N+p−1 samples in the present case. This model then yields $$r = s * \theta + w$$
$$= S \cdot \theta + w$$

with a matrix S having entries $S(j,k)=s(j-k)$, being $s(j)$ the entries of the vector s with $s(j)=0$ for $j<0$, $j \geq N$ (due to the truncation of the first audio signal data 12 mentioned above).

Under the assumption that both the system response θ and the measured neural reaction, i.e., the vector r corresponding to the first measurement data set 12 are Gaussian variables, from a joint Gaussian PDF $$P(r, \theta) = \frac{1}{(2\pi)^{\frac{N+P}{2}}\det^{-1/2}|C|}\exp\left(\frac{-1}{2}\begin{bmatrix}r-E(r)\\\theta-E(\theta)\end{bmatrix}^T C^{-1}\begin{bmatrix}r-E(r)\\\theta-E(\theta)\end{bmatrix}\right)$$

with E(·) being the expectation value and C the covariance matrix $$\begin{bmatrix}C_{rr} & C_{r\theta}\\C_{\theta r} & C_{\theta\theta}\end{bmatrix}$$

of the covariances $C_{r/\theta,r/\theta}$ between the variable vectors r and/or θ, can be defined. It can be shown that from this joint Gaussian PDF, a cPDF for θ given the observation of r can be derived as the (conditional) expectation value $$E(\theta/r)=E(\theta)+C_{\theta r}C_{rr}^{-1}(r-E(r))$$

with the inverse matrix $(·)^{-1}$. The conditional expectation value E(θ|r) of the Gaussian PDF P(r, θ), given the observation of r, is then taken as the Gaussian cPFD. The result for E(θ|r) can be further simplified to $$E(\theta/r)=\mu_\theta+C_{\theta\theta}S^T(SC_{\theta\theta}S^T+C_w)^{-1}(r-S\mu_\theta)$$

with $\mu_\theta$ being the mean value for θ, $C_w$ being the covariance of the noise data set 36 represented in the vector w, and $S^T$ being the transposed matrix of S.

As said mean value is assumed to be zero (otherwise, it might lead to a systematical shift or skewness in the first measurement data set 34), and as the covariance $C_{\theta\theta}$ may be set to the identity matrix by choice of the proper normalization and basis of θ, one finally obtains an estimation for the system response θ of the listener's brain to a sound signal stimulus, which is given by the sound signal stimulus 7 contained in the first sound signal 4. This estimation yields the cPDF:

$$E(\theta/r)=S^T(S\cdot S^T+C_w)^{-1}\cdot r$$

Two key points for estimating the system response θ are the—justified—assumption that the first measurement data set 34 and the system response θ are Gaussian variables, such that the whole toolkit of conditional probabilities is available, and the knowledge of the noise data set 36 in order to determine its covariance matrix $C_w$ required for the cPDF that serves as the estimation of the system response θ.

Figure 4:
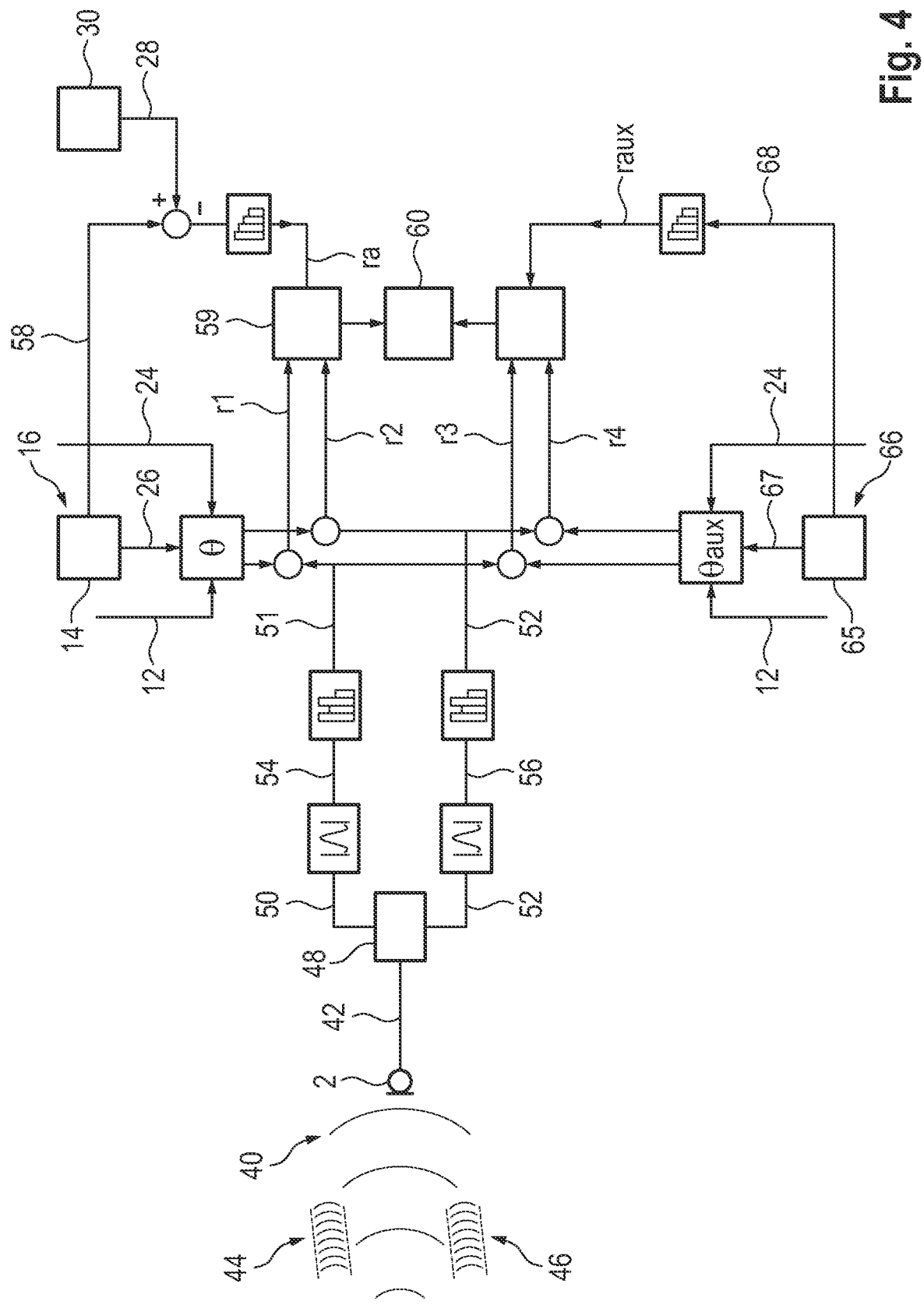
FIG. 4 a block diagram of a method for an AAD of an individual listener's attention to one out of two useful acoustic signals, employing the system response of the listener's brain estimated according to the method display in FIG. 3.

This system response θ of a listener's brain may be used for AAD, which is explained by a respective method displayed in a block diagram shown in FIG. 4. First, system response θ with respect to the first measuring point 16 of the listener's brain is estimated by the method shown in FIG. 3. To this end, the listener is exposed to the first sound signal 4 containing the first sound signal stimulus 7, the first audio signal data 12 is generated from the first sound signal 4, and the first EEG training signal 26 and the noise signal 24 are measured via the first measuring electrode 14 and the reference measuring electrode 30, as well as the noise measuring electrode 18, respectively.

Once the system response θ is known, indicative of which EEG signal to expect at the first measuring point 16 given a particular sound signal, this information is available for use in AAD. To this end, an environment sound 40 that is impinging on an ear of a listener (not shown), is converted to a second audio signal 42 by the first input transducer 2, the environment sound containing a first useful signal 44 and a second useful signal 46. The first useful signal 44 and the second useful signal 46 typically may be given by speech contributions from different speakers, but also other sound signals which might be considered as "useful" to the listener (in the contrast to "sonic noise"), e.g., music played back from a speaker, may be comprised as useful signals.

By audio signal processing 48 containing digitizing the second audio signal 42, signal contributions in the second audio signal 42 corresponding to the first useful signal 44 and the second useful signal 46, are separated from the second audio signal 42, as first signal contributions 50 and second signal contributions 52, respectively. The audio signal processing 48 may contain known processes appropriate to said separation, such as BSS. In case that the second environment sound 40 is converted into a further audio signal by another input transducer (not shown) spaced apart from the first input transducer 2, the audio signal processing also may contain beam forming techniques in order to extract the first and second signal contributions 50, 52, e.g., by directing beams towards the respective sound sources of the first useful signal 44 and the second useful signal 46, or by selectively "muting" their respective signal contributions with help of notch-shaped directional characteristics, directing each of the notches to one of said sound sources.

The first and second signal contributions 50, 52 may be considered, to the extent of the resolution of their separation, as the audio signal corresponding to either the first or second useful signal 44, 46, respectively, without the presence of the other useful signal. The first and second signal contributions 50, 52 are then further processed by extracting the respective first and second useful signal envelopes 54, 56, and by down-sampling at 64 Hz, vectors of first and second useful signal data s1, s2 are generated.

From the first useful signal data vector s1, by using the knowledge of the system response θ, a first reconstructed EEG signal r1 is derived as $$r1=s1*\theta.$$

In a similar way, a second reconstructed EEG signal r2 can be derived from the second useful signal data vector s2 and the system response θ.

While the environment sound 42 containing the first and second useful sounds 44, 46 is impinging on the ear of the listener, also a first EEG application signal 58 is measured by means of the first measuring electrode 14 at the first measuring point 16, and the reference measuring electrode 30 at the reference measuring point R. From said first EEG application signal 58, a data vector ra is extracted by down-sampling, and a correlation analysis 59 is now applied to the data vector ra of said first EEG application signal 58 with respect to each of the first and second reconstructed EEG signals r1 and r2, respectively (note that the first and second reconstructed EEG signals r1 and r2 do not need any further down-sampling, as they have a sample rate of 64 Hz by construction. The correlation analysis may comprise, e.g., the calculation of a respective correlation coefficient for the data vector ra with each of the reconstructed EEG signals r1, r2, or the calculation of a cross correlation for the data vector ra with each of the reconstructed EEG signals r1, r2 and a maximization with respect to the temporal argument of said cross correlations.

Finally, as a result of the AAD, from the correlation analyses it can be determined to which one of the first and second useful signals 44, 46 the listener is directing his attention 60 to. If the correlations between the first reconstructed EEG signal r1 and the data vector ra of the first EEG application signal 58 is higher than the correlation between the second reconstructed EEG signal r2 and the data vector ra (in terms of the correlation measure applied), then it is inferred that the listener is paying attention to the first useful signal 44, and not to the second useful signal 46.

In order to improve the AAD, the described procedure may be additionally performed with respect to a second measuring electrode 65, located at a second measuring point 66 spaced apart from the first measuring point 16. This means that first of all, while the listener is exposed to the first sound signal 4 containing the first sound signal stimulus 7, an auxiliary system response $\theta_{aux}$ of the listener's brain is estimated by the method shown in FIG. 3, by using the first audio signal 12, the noise signal 24, and an auxiliary EEG training signal (67) measured by means of the second measuring electrode 65 located at the second measuring point 66, and the reference measuring electrode 30.

Once this auxiliary system response $\theta_{aux}$ for modeling an EEG at the second measuring point 66 as reaction to a sound signal stimulus 7 is known, from the auxiliary system response $\theta_{aux}$ and the vectors of first and second useful signal data s1 and s2, a third and a fourth reconstructed EEG signal r3, r4, respectively, are generated. While the environment sound 40 containing the first and second useful signals 44, 46 impinges on the listener's ear, an auxiliary EEG application signal 68 is measured by the second measuring electrode 65. In particular, the auxiliary EEG application signal 68 may also be measured by means of the reference measuring electrode 30 (in a way analogous to the AEP 58). From the auxiliary EEG application signal 68, an auxiliary data vector raux is generated by down-sampling, and a correlation analysis 69 for the correlations between said auxiliary data vector raux and either of the third and fourth reconstructed EEG signals r3, r4 is performed. Since the third reconstructed EEG signal r3 is indicative of a potential attention of the listener to the first useful signal 44, the same way as the first reconstructed EEG signal r1, these correlations may also be taken into account for the final result of the AAD.

Figure 5:
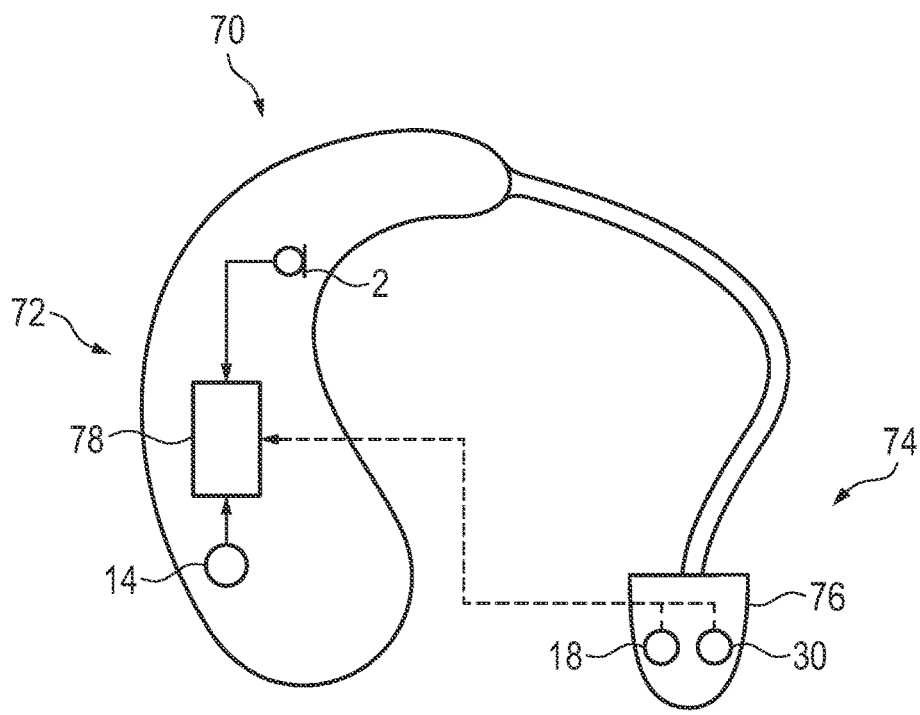
FIG. 5 schematically shows, in a side elevation view, a (BTE) hearing aid configured to perform the estimation method according to FIG. 3, and the AAD method according to FIG. 4.

FIG. 5 schematically shows a lateral view of a hearing aid 70 of the BTE type, comprising a housing given by an ear hook 72, and an earpiece 74 with a mold 76. The ear hook 72 is configured to be worn behind an ear of the hearing aid user (not shown), while the mold 76 is configured to be at least partially inserted into the outer ear channel of said user. The housing of the ear hook 72 contains a first input transducer 2 given by a microphone and connected to a data processing facility 78 given by an appropriate microelectronic device with a CPU and respectively addressed RAM, and a first measuring electrode 14 at a lateral surface of the ear hook 72 and also connected to said data processing facility 78. When the ear hook 72 is worn behind the ear for the hearing aid user, the first measuring electrode 14 is in contact with the hearing aid user's scalp behind the ear.

On the mold 76, on opposite positions of its tip, a reference measuring electrode 30 and a noise measuring electrode 18 are disposed, such that said electrodes are in contact with the skin of the hearing aid user at his outer ear channel, when the mold 76 is worn accordingly. Also the noise measuring electrode 18 and the reference measuring electrode 30 are connected to the data processing facility 78. The data processing facility 78 is configured to estimate the system response $\theta$ of the hearing aid user's brain to a sound signal stimulus from an EEG signal given by the difference of the signals of the first measuring electrode 14 and the reference measuring electrode 30, from a noise signal measured by the noise measuring electrode 18, and from a first audio signal 6 generated by the first input transducer 2 from a corresponding sound signal, as described by the corresponding method in FIG. 3.

Furthermore, the data processing facility 78 is configured to perform the AAD method described in FIG. 4, from an environment sound (not shown in FIG. 5), when said environment sound contains at least two different useful signals, by using an EEG signal given by the difference of the signals of the first measuring electrode 14 and the reference measuring electrode 30, and the first audio signal 6. The data processing facility 78 may also be configured to enhance the useful signal's signal contributions in the first audio signal 6, to which the hearing aid user is directing his attention to, according to the result of the AAD method. This enhancement may be done, e.g., by beam forming, using a further audio signal of a further input transducer (not shown), or by BSS techniques.

Figure 6:
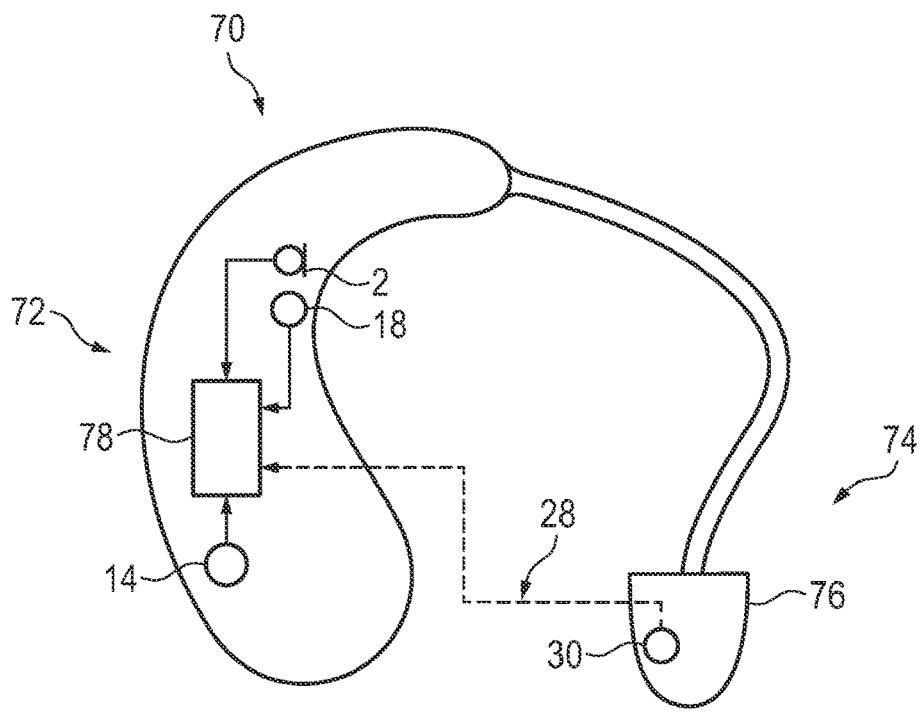
FIG. 6 schematically shows, in a side elevation view, an alternative embodiment of a hearing aid configured to perform the estimation method according to FIG. 3, and the AAD method according to FIG. 4.

FIG. 6 schematically shows an alternative embodiment of the hearing aid 70 given in FIG. 5. Here, the noise measuring electrode 18 is also located on the housing of the ear hook 72. The corresponding noise signal is preferably taken as a difference signal of the signal of the noise measuring electrode 18 and the electrical reference signal 28 measured by the reference measuring electrode 30, located on the tip of the mold 76.

Even though the invention has been illustrated and described in detail with the help of a preferred exemplary embodiment, the invention is not restricted by this example. Other variations can be derived by a person skilled in the art without leaving the extent of protection of this invention.

The following is a summary list of reference numerals and the corresponding structure used in the above description of the invention:

1 AEP
 2 first input transducer
 4 first sound signal
 6 first audio signal
 8 head
 10 first envelope
 12 first audio signal data
 14 first measuring electrode
 16 first measuring point
 18 noise measuring electrode
 20 noise measuring point
 22 first electrical signal
 23 further electrical signal
 24 noise signal
 26 first EEG training signal
 28 electrical reference signal
 30 reference measuring electrode
 34 first measurement data set
 36 noise data set
 40 environment sound
 42 second audio signal
 44 first useful signal
 46 second useful signal
 48 audio signal processing
 50 first signal contributions
 52 second signal contributions
 54 first useful signal envelope
 56 second useful signal envelope
 58 first EEG application signal
 59 correlation analysis
 60 attention
 65 second measuring electrode 66 second measuring point
67 auxiliary EEG training signal
68 auxiliary EEG application signal
69 correlation analysis
70 hearing aid
72 ear hook
74 earpiece
76 mold
78 data processing facility
θ system response
θaux auxiliary system response
C3, C4, Cz measuring point
In measuring point
Na, Nb, N1 negative peak
Pa, P1, P2 positive peak
r data vector (of the first measurement data set)
ra data vector (to the first EEG application signal)
raux data vector (to the auxiliary EEG application signal)
R reference measuring point
r1-r4 first to fourth reconstructed EEG signal
s (vector of) first audio signal data
s1, s2 (vector of) first/second useful signal data
T7, T8 measuring point
w (vector of) noise data

The invention claimed is:

1. A method of estimating a system response of an individual listener's brain to a sound signal stimulus, the system response representing a generation of an electroencephalography signal measured at a given measuring point of the listener's head by the sound signal stimulus, the method comprising:
   presenting a first sound signal containing the sound signal stimulus to an ear of the listener;
   generating a first audio signal corresponding to the first sound signal, and extracting first audio signal data from the first audio signal;
   using a first measuring electrode at said given measuring point on the listener's head for measuring a first electroencephalography training signal while the first sound signal containing the sound signal stimulus impinges on the ear of the listener, and generating a first measurement data set from the first electroencephalography training signal;
   using a noise measuring electrode at a noise measuring point on the listener's head for measuring a noise signal while the first sound signal impinges on the ear of the listener, and generating a noise data set from the noise signal;
   deriving from the first measurement data set and the noise data set a Gaussian conditional probability density function for the system response of the listener's brain to the first audio signal data, given an observation of the first measurement data set; and
   taking the Gaussian conditional probability density function as the system response of the listener's brain to the sound signal stimulus, with respect to the given measurement point.

2. The method according to claim 1, which comprises extracting a first envelope as the envelope of the first audio signal, and deriving the first audio signal data, from the first envelope.

3. The method according to claim 2, wherein the first audio signal data is derived from the first envelope employing a down-sampling process.

4. The method according to claim 1, which comprises generating the first measurement data set from the first electroencephalography training signal employing a down-sampling process, and/or generating the noise data set from the noise signal employing a down-sampling process.

5. The method according to claim 1, which comprises deriving the Gaussian conditional probability density function for the system response of the listener's brain to the first audio signal data, given the observation of the first measurement data set, from a Gaussian joint probability density function for the system response of the listener's brain and the first measurement data set.

6. The method according to claim 5, wherein the Gaussian conditional probability density function for the system response of the listener's brain to the first audio signal data, given the observation of the first measurement data set, is given by an expectation value of the form $$E(\theta/r)=\mu_\theta+C_{\theta\theta}S^T(SC_{\theta\theta}S^T+C_w)^{-1}(r-S\mu_\theta)$$

where
   $E(\cdot)$ denotes the expectation value;
   r denotes the principal data set;
   θ denotes the system response of the listener's brain to the sound stimulus contained in the first audio signal data represented by a vector s;
   $\mu_\theta$ and $C_{\theta\theta}$ denotes the expectation value $E(\theta)$ and covariance matrix of θ, respectively;
   Cw denotes the covariance matrix of the noise data set w; and
   S denotes a matrix constructed such that the vector resulting from the product S·θ, entry by entry, represents a convolution of the vectors s and θ for different time arguments.

7. The method according to claim 1, which comprises:
   using a plurality of sound signal stimuli in order to generate a set of preliminary Gaussian conditional probability density functions, each of which is estimated by employing the method according to claim 1 and by using a different sound signal stimulus out of the plurality; and
   deriving the system response of the listener's brain to a sound signal stimulus, with respect to the given measurement point, from an arithmetic mean of the preliminary Gaussian conditional probability density functions.

8. A method for an auditory attention decoding of an individual listener's attention to one of a plurality of signals including at least a first useful signal and a second useful signal, the method comprising:
   exposing an ear of the listener to a first sound signal containing a sound signal stimulus;
   measuring a first electroencephalography training signal with a measuring electrode disposed at a given measuring point, and estimating a system response of the listener's brain to the sound signal stimulus with respect to the given measuring point from the first electroencephalography training signal, carrying out the estimating step by performing the method according to claim 1;
   converting an environment sound containing at least the first useful signal and the second useful signal at the ear of the listener into a second audio signal;
   extracting first signal contributions of the first useful signal from the second audio signal;
   extracting second signal contributions of the second useful signal from the second audio signal;
   deriving from the system response of the listener's brain and the first signal contributions, a first reconstructed electroencephalography signal;

deriving from the system response of the listener's brain and the second signal contributions, a second reconstructed electroencephalography signal;

while the environment sound is impinging on the listener's ear, measuring a first electroencephalography application signal by way of the measuring electrode located at the given measurement point; and inferring the listener's attention to either the first useful signal or the second useful signal from correlations between the first electroencephalography application signal and the first reconstructed electroencephalography signal and from correlations between the first electroencephalography application signal and the second reconstructed electroencephalography signal.

9. The method according to claim 8, which comprises:

extracting from the first signal contributions of the first useful signal a first useful signal envelope, and deriving the first reconstructed electroencephalography signal from the system response of the listener's brain and the first useful signal envelope; and/or extracting from the second signal contributions of the second useful signal a second useful signal envelope, and deriving the second reconstructed electroencephalography signal from the system response of the listener's brain and the second useful signal envelope.

10. The method according to claim 8, which comprises:

estimating an auxiliary system response of the listener's brain to a sound signal stimulus with respect to a second measuring point at the listener's head by way of an auxiliary electroencephalography training signal measured with a second measuring electrode disposed at a second measuring point, the estimation being performed using the method according to claim 1, the sound signal stimulus being contained in the first sound signal;

deriving from the auxiliary system response of the listener's brain and the first signal contributions of the first useful signal, a third reconstructed electroencephalography signal;

deriving from the auxiliary system response of the listener's brain and the second signal contributions of the second useful signal, a fourth reconstructed electroencephalography signal;

while the environment sound is impinging on the listener's ear, measuring an auxiliary electroencephalography application signal by means of a measuring electrode located at said second measurement point, and inferring the listener's attention to either the first useful signal or the second useful signal taking into account correlations between the auxiliary electroencephalography application signal and the third reconstructed electroencephalography signal, and correlations between the auxiliary electroencephalography application signal and the fourth reconstructed electroencephalography signal.

11. A hearing system, comprising a hearing aid having:

at least a first input transducer configured to convert a first sound signal into a first audio signal and/or at least a first output transducer to generate a first sound signal from a first audio signal;

a first measuring electrode configured to measure a first electrical signal at a hearing aid user's head, the first electrical signal being indicative of a first electroencephalography training signal stimulated by a sound signal stimulus contained in the first sound signal;

a noise measuring electrode configured to measure, at the hearing aid user's head, a further electrical signal indicative of a noise signal with respect to the first electroencephalography training signal;

a data processing facility configured to derive the first electroencephalography training signal from the first electrical signal, to derive the noise signal from the further electrical signal, and to process the first audio signal;

said data processing facility being further configured to estimate the system response of the hearing aid user's brain to the sound signal stimulus contained in the first sound signal by employing the method according to claim 1, the estimation using the first audio signal, the first electroencephalography training signal, and the noise signal.

12. The hearing system according to claim 11, wherein said data processing facility is further configured to derive a first electroencephalography application signal from the first electrical signal, and to perform the method for auditory attention decoding of the hearing aid user's attention to one out of at least a first useful signal and a second useful signal according to claim 8 by using the first electroencephalography application signal, when an environment sound containing the first useful signal and the second useful signal is converted into the first audio signal.

13. The hearing system according to claim 12, wherein said data processing facility is further configured to process the first audio signal by enhancing the first signal contributions when the auditory attention decoding as a result yields the hearing aid user's attention to the first useful signal.

14. The hearing system according to claim 11, wherein:

said hearing aid further comprises a reference measuring electrode, configured to measure an electrical reference signal at a reference measuring point on the listener's head;

said data processing facility is configured to derive the first electroencephalography training signal and/or the first electroencephalography application signal from the first electrical signal and the electrical reference signal; and/or the noise signal is derived from the further electrical signal of said noise measuring electrode and the electrical reference signal.

15. The hearing system according to claim 11, wherein:

said hearing aid further comprises an ear hook configured to be worn at least partially behind the pinna for the ear and an earpiece with a mold configured to be at least partially inserted into the concha and/or outer ear channel of an ear of the hearing aid user; and said first measuring electrode is disposed on said ear hook such that the first measuring electrode is in contact with the hearing aid user's scalp when said ear hook is worn at least partially behind the pinna.

16. The hearing system according to claim 15, wherein said noise measuring electrode is disposed on a mold of said hearing aid such that said noise measuring electrode is in contact with the skin of the concha or the outer ear channel when said mold is inserted as intended.

17. The hearing system according to claim 15, wherein said noise measuring electrode is disposed on said ear hook of said hearing aid, spatially separated from said first measuring electrode and such that said noise measuring electrode is in contact with the hearing aid user's scalp when said ear hook is worn at least partially behind the pinna.

18. The hearing system according to claim 15, wherein:
said hearing aid further comprises a reference measuring electrode, configured to measure an electrical reference signal at a reference measuring point on the listener's head;
said data processing facility is configured to derive the first electroencephalography training signal and/or the first electroencephalography application signal from the first electrical signal and the electrical reference signal; and/or
the noise signal is derived from the further electrical signal of said noise measuring electrode and the electrical reference signal; and
wherein said reference measuring electrode is disposed on a mold of said hearing aid such that said reference measuring electrode is in contact with the skin of the concha or the outer ear channel when said mold is inserted as intended.

* * * * *